(12) United States Patent
Schindler

(10) Patent No.: US 9,776,194 B2
(45) Date of Patent: Oct. 3, 2017

(54) FROTH FLOTATION SEPARATION AND ANALYSIS

(71) Applicant: Heraeus Quartz UK Limited, Tyne and Wear (GB)

(72) Inventor: Michael Schindler, Newcastle upon Tyne (GB)

(73) Assignee: Heraeus Quartz UK Limited, Tyne and Wear (GB)

( * ) Notice: Subject to any disclaimer, the term of this patent is extended or adjusted under 35 U.S.C. 154(b) by 219 days.

(21) Appl. No.: 14/779,054

(22) PCT Filed: May 9, 2014

(86) PCT No.: PCT/GB2014/051437
§ 371 (c)(1),
(2) Date: Sep. 22, 2015

(87) PCT Pub. No.: WO2014/184523
PCT Pub. Date: Nov. 20, 2014

(65) Prior Publication Data
US 2016/0051993 A1    Feb. 25, 2016

(30) Foreign Application Priority Data

May 13, 2013  (GB) .................................. 1308576.6

(51) Int. Cl.
*B03D 1/02* (2006.01)
*B03D 1/08* (2006.01)
*C03C 1/02* (2006.01)

(52) U.S. Cl.
CPC .............. *B03D 1/087* (2013.01); *B03D 1/02* (2013.01); *C03C 1/022* (2013.01); *B03D 2203/005* (2013.01)

(58) Field of Classification Search
None
See application file for complete search history.

(56) References Cited

U.S. PATENT DOCUMENTS

| | | | | |
|---|---|---|---|---|
| 2,409,665 A | * | 10/1946 | Cole | ........................ B03D 1/02 |
| | | | | 209/166 |
| 2,433,633 A | * | 12/1947 | Stokes | .................... C03C 1/022 |
| | | | | 209/166 |
| 4,401,638 A | * | 8/1983 | Caballero | ................. B03B 9/00 |
| | | | | 209/166 |
| 4,725,351 A | | 2/1988 | Mehrotra | |
| 4,804,422 A | | 2/1989 | Papanikolau et al. | |
| 4,983,370 A | | 1/1991 | Loritsch et al. | |
| 5,037,625 A | | 8/1991 | Loritsch et al. | |
| 5,102,837 A | | 4/1992 | Balkany et al. | |
| 5,311,997 A | | 5/1994 | Gantt et al. | |
| 5,358,120 A | | 10/1994 | Gantt et al. | |
| 5,735,928 A | | 4/1998 | Sayce et al. | |
| 5,914,034 A | | 6/1999 | Ding et al. | |
| 5,928,125 A | | 7/1999 | Ding et al. | |
| 5,985,779 A | | 11/1999 | Sayce et al. | |
| 6,059,118 A | | 5/2000 | Ding et al. | |
| 6,126,836 A | | 10/2000 | Ding et al. | |
| 6,763,682 B1 | | 7/2004 | Sayce et al. | |
| 8,959,957 B2 | | 2/2015 | Coapes et al. | |
| 2007/0271964 A1 | | 11/2007 | Huenermann | |
| 2009/0104454 A1 | | 4/2009 | Sayce | |
| 2012/0103017 A1 | | 5/2012 | Ludwig | |
| 2013/0115391 A1 | | 5/2013 | Coapes et al. | |
| 2014/0106094 A1 | | 4/2014 | Mundy et al. | |
| 2015/0135772 A1 | | 5/2015 | Mundy et al. | |

FOREIGN PATENT DOCUMENTS

| | | |
|---|---|---|
| AT | 406739 B | 8/2000 |
| CN | 101293222 A | 10/2008 |
| GB | 462213 A | 4/1937 |
| JP | H02-164740 A | 6/1990 |
| WO | 00/24918 A1 | 5/2000 |
| WO | 2010/004941 A1 | 1/2010 |

OTHER PUBLICATIONS

R. McEwen et al., "Single-Stage Flotation of Alkali Feldspar, Limenite, Rutile, Garnet, and Monazite, with Mixed Catonic/Anionic Collectors", Society of Mining Engineers, AIME, vol. 260, pp. 97-100, Mar. 1976.

* cited by examiner

*Primary Examiner* — Thomas M Lithgow
(74) *Attorney, Agent, or Firm* — Howson & Howson LLP

(57) ABSTRACT

A method of separating heavy mineral particles, such as zircon, monazites, xenotime etc., from a sample of quartz crystal powder, comprises the steps of:
  a. conditioning the quartz powder suspected of containing heavy mineral particles as an aqueous pulp using a froth-flotation agent;
  b. subjecting the conditioned pulp to froth flotation to obtain a tailing;
  c. combining the tailing with an aqueous solution having a density greater than that of quartz and less than that of a heavy mineral which it is desired to separate; and
  d. centrifuging the combination.

The separated heavy mineral crystals can then be characterized using a micro-analysis technique.

19 Claims, No Drawings

FROTH FLOTATION SEPARATION AND ANALYSIS

BACKGROUND TO THE INVENTION

This invention relates to a method of separating heavy minerals from a quartz powder and a method of analysing heavy minerals contained in a quartz powder.

In the present context the term "heavy minerals" includes, without limitation, zircon (zirconium silicate), monazites of all kinds (mixed rare earth phosphates), especially xenotime (a mineral containing yttrium phosphate). In addition to rare earth metals they may include low levels of radioactive metals such as thorium and uranium. Such minerals may be present in relatively small quantities (less than 1 ppm) in bulk quartz crystal powders, but they have proved difficult to remove by methods standard in the industry, and even such low levels are undesirable in transparent fused quartz glass products.

Commercial suppliers of high purity quartz powder may produce their powders from a variety of raw materials, and these sources may include pegmatites, i.e. coarse-grained granitic igneous rock. These typically comprise an intimate mixture of feldspars, mica and quartz crystals as well as a diverse range of heavy minerals. By such processes as crushing, leaching, froth flotation etc. a considerable degree of refinement of the quartz is possible, indeed froth flotation is a standard technique in the industry. McEwen et al, "Single-Stage Flotation of Alkali Feldspars, Ilmenite, Rutile, Garnet, and Monazite, with Mixed Cationic/Anionic Collectors", *Society of Mining Engineers, AIME*, vol. 260, pp 97-100 (1976), describes the flotation of feldspar and other heavy minerals from quartz using cationic and/or anionic collectors. However, these techniques do not provide complete separation of contaminating species, and many smaller crystals of heavy minerals remain in the quartz powder and are not removed by conventional methods of quartz refinement.

Thus commercially available refined quartz powders have been found to contain heavy mineral particles, typically in the range 5-50 µm in size. Despite the apparently low analytical concentration they exist in large numbers, and are a potential source of defects, some visible with the naked eye and some fluorescing under UV light. In fused quartz glass these particles may dissolve to form a locally contaminated region; they may not dissolve entirely, in which case they may form a local region of phase-separated glass; they may act as nuclei for devitrification of the glass, when typically they may be found at the centre of a roughly spherical region of cristobalite, and finally some of these defects may be found to be associated with a small bubble of gas, which has been liberated by decomposition of the contaminating particle.

Some of these defects would render the glass unsuitable for certain optical applications, and they would also be undesirable in many quartz glass products for the semiconductor industry. When incorporated in a fused quartz crucible as used in the growth of silicon crystal there is the possibility of detachment of a particle leading to contamination of the silicon melt. When present in a fused silica semiconductor jig or window, which may be subject to etching in the course of its use, there is the possibility of detachment of a particle which may be transferred to the surface of the silicon wafer being processed, causing an irreparable defect in a circuit. Where the particle is radioactive, there is the possibility of longer range damage to the semiconductor product. Conventional chemical analysis is an unreliable measure of the content of heavy minerals, many of which are insoluble under normal analytical conditions. Even when chemical analysis is accurate it may not provide a reliable indication of the number of point defects likely to be generated in a transparent glass product.

In gauging the suitability of a given powder for the manufacture of a high quality fused quartz product it is important to be able to assess the number and size of these particulate contaminants, however past analytical techniques have proved to be inadequate.

In mineralogy in general, specific gravity methods have been used for heavy mineral separation. Halogenated hydrocarbon liquids such as bromoform and tetrabromomethane are used in standard glass separating funnels. These methods suffer from a number of disadvantages. Heavy mineral grains are retained on the glass walls of the funnel by electrostatic attraction. The minerals can also be trapped by the quartz grains and prevented from settling. The mineral grains can additionally be entrapped between the stop-cock sliding surfaces. Sealing times in such a separation are prolonged, and for particles in the size range of interest range from many hours to several days, or longer. Finally the liquids which have been used are toxic, and may be absorbed through the skin, or by inhalation of the vapour.

SUMMARY OF THE INVENTION

An aim of the present invention is to separate sub part per million by number (and low ppb levels by weight) occurrences of fine particle heavy minerals from samples of quartz powder, more efficiently than by any known method, and thereby to permit the accurate identification and quantification of the various contaminants.

The present invention provides a method of separating heavy mineral particles from a sample of quartz crystal powder, comprising the steps of:
  a. conditioning the quartz powder suspected of containing heavy mineral particles as an aqueous pulp using promoter froth-flotation agent;
  b. subjecting the conditioned pulp to froth flotation to obtain a tailing; and
  c. combining the tailing with an aqueous solution having a density greater than that of quartz and less than that of a heavy mineral which it is desired to separate; and
  d. centrifuging the combination in the vessel.

The froth-flotation agent may comprise an anionic promoter, in particular a petroleum based sulphonate promoter. The pH of the aqueous pulp may be controlled, for example to be acidic, in particular between 2 and 3.5, more particularly between 2.5 and 3. The promoter may be added in a dosage of between 0.5 and 5 ml per kilogram of quartz powder, preferably between 1 and 3 ml.

The quartz powder has a particle size of between 25 and 1000 µm, preferably between 50 and 500 µm, and the heavy mineral particles in question are typically of particle size in the range 5-50 µm.

During conditioning, the pulp may be 65 to 75% solids by weight, preferably 68 to 72% solids by weight. Conditioning may take place for 5 to 20 minutes, preferably 5 to 10 minutes.

During froth flotation, the pulp may be 10 to 30% solids by weight, preferably 20 to 25% solids by weight. Froth flotation may take place for 5 to 60 minutes, preferably for 5 to 30 minutes.

The aqueous solution may be a solution of one or more polytungstates or heteropolytungstates, in a particular an alkaline metal polytungstate such as sodium heteropolytungstate and may have a density of 2.68 to 2.95 g/cm³, preferably 2.70 to 2.85 g/cm³. A floating layer primarily of quartz in the centrifuged product may be agitated, and centrifuging repeated.

The laboratory centrifuge used to aid settlement of the heavy mineral particles may operate at 200-1000 rpm, exerting a relative centrifugal acceleration of 5-100 g. A typical laboratory centrifuge operates at 600 rpm, exerting a relative centrifugal acceleration of 50 g on each sample. A non-vitreous centrifuging vessel may be used.

The invention also provides a method of analysing heavy minerals present in a quartz powder, comprising the steps of separating the heavy minerals using the method described above; and characterising the separated heavy mineral crystals using an appropriate technique, such as for example optical and/or Raman microscopy, Energy Dispersive Analysis by X-ray (EDAX), X-ray Diffraction (XRD), X-ray Fluorescence (XRF), Laser Mass-spectrometry, etc. Generally optical microscopy provides a convenient analytical tool permitting identification of the more comment heavy minerals. However, zircon and xenotime have similar optical and crystallographic properties and are frequently counted together.

The present technique has been used together with appropriate analytical techniques to separate and subsequently identify particles of each of the contaminating species shown in Table 1 below, in batches of refined quartz crystal being prepared for fusion to quartz glass.

TABLE 1

|  |  | S.G. | Typical size (μm) |
|---|---|---|---|
| Mineral Particles derived from quartz | | | |
| Apatite | Calcium phosphate | 3.16-3.22 | 10-20 |
| Barytes | Barium Sulphate | 4.3-5 | 10-40 |
| Biotite | Potassium (magnesium etc.) aluminium silicate | 2.7-3.1 | 40-80 |
| Epidote | Calcium aluminium silicate | 3.3-3.6 | 40-100 |
| Garnet - Almandine | Iron aluminium silicate | 4.05 | 20-60 |
| Garnet - Spessartine | Manganese aluminium silicate | 4.12-4.32 | 20-60 |
| Gold | Native gold | 19.3 | 5-30 |
| Monazites | Mixed rare earth phosphates - may include thorium | 4.6-5.7 | 5-60 |
| Pyrite | Iron sulphide | 4.8-5.0 | 10-50 |
| Rutile | Titanium dioxide | 4.23 | 10-50 |
| Thorite | Thorium uranium silicate | 6.63-7.2 | 10-30 |
| Tourmalines | Boron-containing complex silicates | 2.82-3.32 | 20-60 |
| Xenotime | Yttrium phosphate | 4.4-5.1 | 10-50 |
| Zircon | Zirconium silicate | 4.6-4.7 | 5-80 |
| Ilmenite | Iron Titanium oxide | 4.7-4.8 | 10-50 |
| Impurity particles due to processing | | | |
|  | Iron oxide (rust) | 5.24 | 10-100 |
|  | Silicon carbide | 3.21 | 30-150 |
|  | Tramp metal, weld spheres (e.g. iron) | 7.87 | 5-80 |
|  | Manganese steel | 7.7-7.9 | 5-80 |
|  | Stainless steel | 7.7-7.9 | 10-100 |

DETAILED DESCRIPTION OF PARTICULAR EMBODIMENTS

The invention will now be described in more detail by way of example only.

A weighed sample (1500 g) of commercially available quartz powder, sold for the manufacture of high grade fused quartz products, was taken and conditioned for 6 minutes as an aqueous acidic pulp using Aerofloat® 869F, from Cytec Corporation, an anionic petroleum based sulfonate promoter, containing a frothing agent, at a dosage of 2.5 ml of promoter per kilogram of quartz. The conditioned pulp had a density of approximately 71% solids by weight.

The conditioned pulp was subjected to reverse froth flotation in a supercharged flotation cell, for a period of 25 minutes, to obtain quartz tailings (a float fraction) containing a high concentration of heavy mineral grains, which were carried over in the overflowing froth The tailings were collected in a beaker, washed using acetone, dried, cooled and then suspended in LST Fastfloat from Pangea UK, a low-viscosity aqueous salt solution prepared using sodium heteropolytungstate and having a density (i.e. specific gravity) of about 2.82 g/cm³, in a plastic tube. Other alkali metal polytungstates and heteropolytungstates, such as lithium heteropolytungstate, have a similar specific gravity and could alternatively be used. Note that the specific gravity of quartz is approximately 2.65 g/cm³.

The tube was centrifuged in a laboratory centrifuge to obtain a floating layer of quartz powder and a sediment of heavy minerals. Complete separation was not achieved in a first centrifugation as some heavy minerals were entrained in the quartz powder. This layer was carefully stirred within the plastic tube, without disturbing the contents below. A further three centrifugations and stirrings of the quartz fraction were carried out alternately.

The supernatant liquid was removed and the fine particle heavy mineral residue was washed first with deionised water and then with industrial methylated spirit (IMS) with intermediate centrifugation. The IMS suspension was finally removed with a pipette, deposited on a microscope slide and the liquid was allowed to dry. The particles were then viewed under an optical microscope, permitting an estimate to be made of the number of particles and a preliminary assessment of their constitution. Monazite grains could be distinguished by their orange or brown colour. In order to distinguish between grains of zircon and xenotime, Raman spectroscopy, EDAX or an X-ray diffraction technique could be employed. Counts of the numbers of grains of each heavy mineral could be made, and numbers per kilogram of quartz powder estimated.

Examples of analyses for four different samples of quartz powder are set out below. These powders were of particle size nominally 75 to 150 μm, and were supplied by a commercial source of high purity quartz powders, of a quality intended for the manufacture of fused silica for semiconductor applications.

EXAMPLE 1

|  |  | Approx. ppm | |
|---|---|---|---|
| Mineral | Particles/kg | by number | by weight |
| Zircon/Xenotime | 11900 | 12 | 1.9 |
| Monazite | 1200 | 1.2 | 0.2 |
| Gold | 47 | 0.05 | 0.03 |

EXAMPLE 2

| Mineral | Particles/kg | Approx. ppm by number | by weight |
|---|---|---|---|
| Zircon/Xenotime | 3300 | 3.3 | 0.53 |
| Monazite | 200 | 0.2 | 0.035 |
| Gold | 27 | 0.027 | 0.017 |
| Silicon Carbide | 14 | 0.014 | 0.002 |

EXAMPLE 3

| Mineral | Particles/kg | Approx. ppm by number | by weight |
|---|---|---|---|
| Zircon/Xenotime | 11100 | 11.1 | 1.2 |
| Monazite | 900 | 0.9 | 0.16 |
| Silicon Carbide | 14 | 0.014 | 0.002 |
| Rust | 40 | 0.04 | 0.04 |
| Ferrous Metal | 20 | 0.02 | 0.005 |

EXAMPLE 4

| Mineral | Particles/kg | Approx. ppm by number | by weight |
|---|---|---|---|
| Zircon/Xenotime | 9700 | 9.7 | 1.54 |
| Monazite | 340 | 0.34 | 0.059 |
| Silicon Carbide | 7 | 0.007 | 0.001 |
| Rust | 110 | 0.1 | 0.2 |
| Ferrous Metal | 180 | 0.18 | 0.03 |

The invention has thus enabled the detection, quantification and analysis of small amounts of fine particle heavy minerals in quartz powder and thus an assessment of the quality of the powder and its potential for the manufacture of transparent fused quartz. Until the present analytical method was developed the number of such heavy mineral particles was either unknown, or grossly underestimated.

The invention claimed is:

1. A method of separating heavy mineral particles from a sample of quartz crystal powder, comprising the steps of:
   a. conditioning the quartz powder suspected of containing heavy mineral particles as an aqueous pulp using a froth-flotation agent;
   b. subjecting the conditioned pulp to froth flotation to obtain a tailing;
   c. combining the tailing with an aqueous solution having a density greater than that of quartz and less than that of a heavy mineral which it is desired to separate; and
   d. centrifuging the combination.

2. A method of analysing heavy minerals present in a quartz powder, comprising the steps of separating the heavy minerals using a method according to claim 1; and characterising the separated heavy mineral crystals using a microanalysis technique.

3. A method according to claim 2, wherein the microanalysis technique comprises at least one of optical microscopy, Raman microscopy, Energy Dispersive Analysis by X-ray (EDAX), X-ray Diffraction (XRD), X-ray Fluorescence (XRF), or Laser Mass-spectrometry.

4. A method according to claim 1, wherein the aqueous pulp is pH-controlled.

5. A method according to claim 4, wherein the aqueous pulp is acidic.

6. A method according to claim 1, wherein the froth-flotation agent comprises an anionic promoter.

7. A method according to claim 6, wherein the anionic promoter is a petroleum based sulphonate promoter.

8. A method according to claim 1, wherein the aqueous pulp has a pH of between 2 and 3.5.

9. A method according to claim 6, wherein the promoter is added in a dosage of between 0.5 and 5 ml per kilogram of quartz powder.

10. A method according to claim 1, wherein the quartz powder has a particle size of between 25 and 1000 μm.

11. A method according to claim 1, wherein during conditioning the pulp is 65 to 75% solids by weight.

12. A method according to claim 1, wherein conditioning takes place for 5 to 20 minutes.

13. A method according to claim 1, wherein during froth flotation, the pulp is 10 to 30% solids by weight.

14. A method according to claim 1, wherein flotation takes place for 5 to 60 minutes.

15. A method according to claim 1, wherein the aqueous solution is a solution of one or more alkali metal polytungstates or heteropolytungstates.

16. A method according to claim 1, wherein the aqueous solution is a solution of sodium heteropolytungstate.

17. A method according to claim 1, wherein the aqueous solution has a density of 2.68 to 2.95 g/cm$^3$.

18. A method according to claim 1, wherein a non-vitreous vessel is used for centrifuging in step (d).

19. A method according to claim 1, including the step of agitating a floating layer primarily of quartz in the centrifuged product, and re-centrifuging.

* * * * *